(12) United States Patent
Park

(10) Patent No.: US 9,004,339 B1
(45) Date of Patent: Apr. 14, 2015

(54) CARTRIDGIZABLE FEEDER BELT FOR SURGICAL STAPLER

(75) Inventor: Jinhoon Park, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 1210 days.

(21) Appl. No.: 12/471,672

(22) Filed: May 26, 2009

(51) Int. Cl.
*A61B 17/04* (2006.01)
*A61B 17/10* (2006.01)
*A61B 17/068* (2006.01)

(52) U.S. Cl.
CPC .................................. *A61B 17/068* (2013.01)

(58) Field of Classification Search
USPC ............... 275/175.1–181.1; 227/175.1–182.1
See application file for complete search history.

(56) References Cited

U.S. PATENT DOCUMENTS

| | | | |
|---|---|---|---|
| 3,581,551 A | | 6/1971 | Wilkinson |
| 3,650,453 A | * | 3/1972 | Smith, Jr. ...................... 227/138 |
| 3,899,914 A | | 8/1975 | Akiyama |
| 4,060,089 A | * | 11/1977 | Noiles ............................ 606/220 |
| 4,086,926 A | * | 5/1978 | Green et al. ................... 606/143 |
| 4,127,227 A | * | 11/1978 | Green ............................. 227/83 |
| 4,228,895 A | | 10/1980 | Larkin |
| 4,475,679 A | | 10/1984 | Fleury, Jr. |
| 4,589,416 A | | 5/1986 | Green |
| 4,633,861 A | | 1/1987 | Chow et al. |
| 4,762,260 A | | 8/1988 | Richards et al. |
| 4,969,591 A | | 11/1990 | Richards et al. |
| 5,156,315 A | | 10/1992 | Green et al. |
| 5,192,288 A | | 3/1993 | Thompson et al. |
| 5,413,272 A | | 5/1995 | Green et al. |
| 5,476,206 A | | 12/1995 | Green |
| 5,655,698 A | | 8/1997 | Yoon |
| 5,662,260 A | | 9/1997 | Yoon |
| 5,692,668 A | | 12/1997 | Schulze et al. |
| 5,810,855 A | | 9/1998 | Rayburn et al. |
| 5,816,471 A | | 10/1998 | Plyley et al. |
| 5,833,695 A | * | 11/1998 | Yoon ............................. 606/139 |
| 5,855,311 A | | 1/1999 | Hamblin et al. |
| 5,894,979 A | | 4/1999 | Powell |
| 5,918,791 A | | 7/1999 | Sorrentino et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory* 39(2004), (Nov. 2004),1155-1174.

(Continued)

*Primary Examiner* — Robert Long
(74) *Attorney, Agent, or Firm* — Cardica, Inc.

(57) ABSTRACT

An exemplary surgical apparatus may include a feeder belt lying substantially in a single plane; and staples fixed to and frangibly separable from the feeder belt. A cartridge may hold at least one feeder belt, where that cartridge may be detachably held by a receiver. The cartridge itself may be reloadable. A surgical method may include providing a surgical instrument including a detachable cartridge holding a feeder belt, where staples are fixed to and frangibly separable from the feeder belt; deforming at least one staple to a deformed state; frangibly separating at least one deformed staple from the feeder belt; and removing the cartridge from the surgical instrument.

15 Claims, 4 Drawing Sheets

(56) References Cited

U.S. PATENT DOCUMENTS

| | | | |
|---|---|---|---|
| 5,964,774 A | 10/1999 | McKean et al. | |
| 6,306,149 B1 | 10/2001 | Meade | |
| 6,391,038 B2 * | 5/2002 | Vargas et al. | 606/153 |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,918,376 B1 * | 4/2011 | Knodel et al. | 227/175.1 |
| 7,954,683 B1 * | 6/2011 | Knodel et al. | 227/175.1 |
| 7,963,432 B2 * | 6/2011 | Knodel et al. | 227/175.1 |
| 7,988,026 B2 * | 8/2011 | Knodel et al. | 227/175.1 |
| 2003/0035702 A1 * | 2/2003 | Lin | 411/442 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2009/0065552 A1 * | 3/2009 | Knodel et al. | 227/180.1 |
| 2010/0230464 A1 * | 9/2010 | Knodel et al. | 227/175.1 |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg. 60*(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

"Cardica Microcutter Implant Delivery Device 510(k), Cover Sheet, Table 10.1, "Substantial Equivalence Comparison," and Section 12, "Substantial Equivalence Discussion"".

* cited by examiner

CARTRIDGIZABLE FEEDER BELT FOR SURGICAL STAPLER

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient.

BRIEF DESCRIPTION OF THE DRAWINGS

The use of the same reference symbols in different figures indicates similar or identical items.

DETAILED DESCRIPTION

Figure 1:
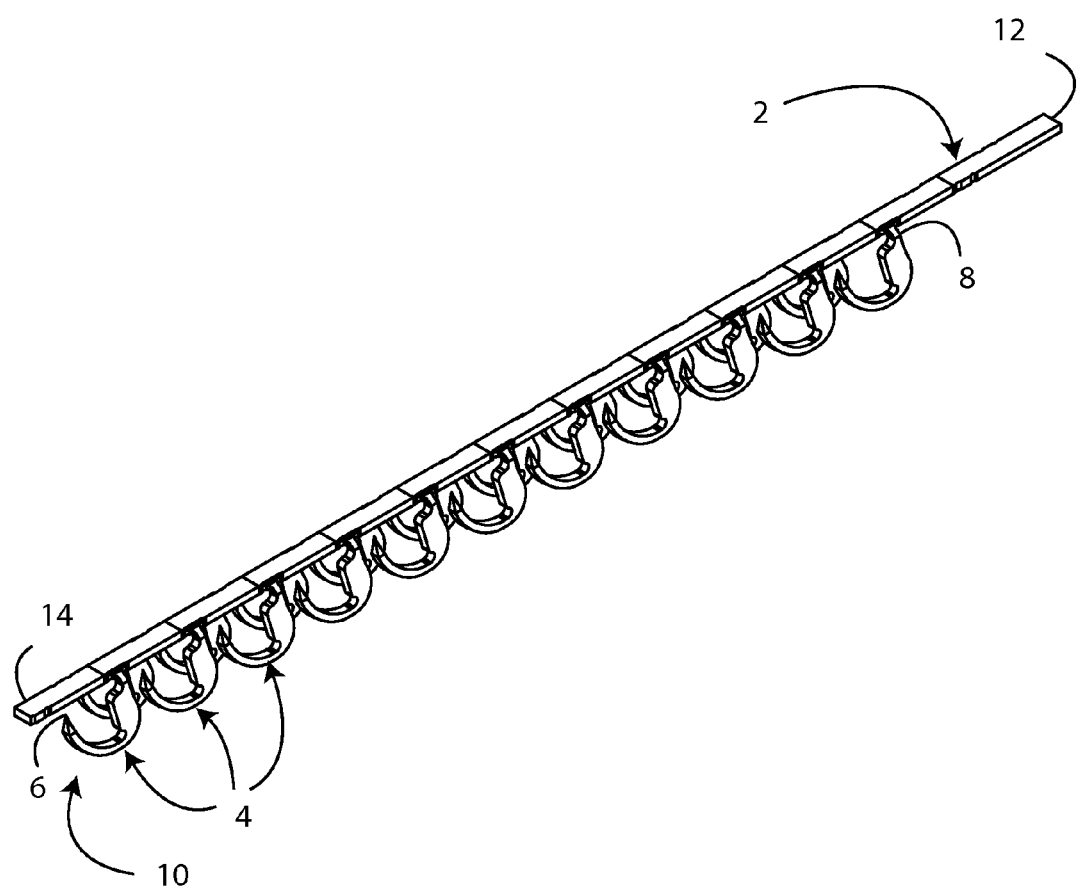
FIG. 1 is a perspective view of an exemplary feeder belt.

U.S. patent application Ser. No. 12/263,171, filed on Oct. 31, 2008 (the "Endocutter Document"), is hereby incorporated by reference herein in its entirety. The Endocutter Document describes exemplary feeder belts used in a surgical stapler. Referring to FIG. 1, a feeder belt 2 may be a long, narrow, thin strip of material from which one or more staples 4 extend. The feeder belt 2 and staples 4 of the present document may be substantially as set forth in the Endocutter Document, with the exception of the inventive features set forth in the present document. Each staple 4 may have a free end 6, and an opposite end 8 that is connected to the feeder belt 2. Advantageously, the staples 4 are frangibly affixed to the feeder belt 2, such that they are sheared off from the feeder belt 2 during deployment. However, the staples 4 may be connected to the feeder belt 2 in any suitable manner. One or more rows 10 of staples 4 may be connected to the feeder belt 2. Each row 10 of staples 4 is the group of staples 4 positioned at substantially the same lateral location relative to the longitudinal centerline of the feeder belt 2, and each row 10 of staples 4 may be oriented generally longitudinally.

Figure 2:
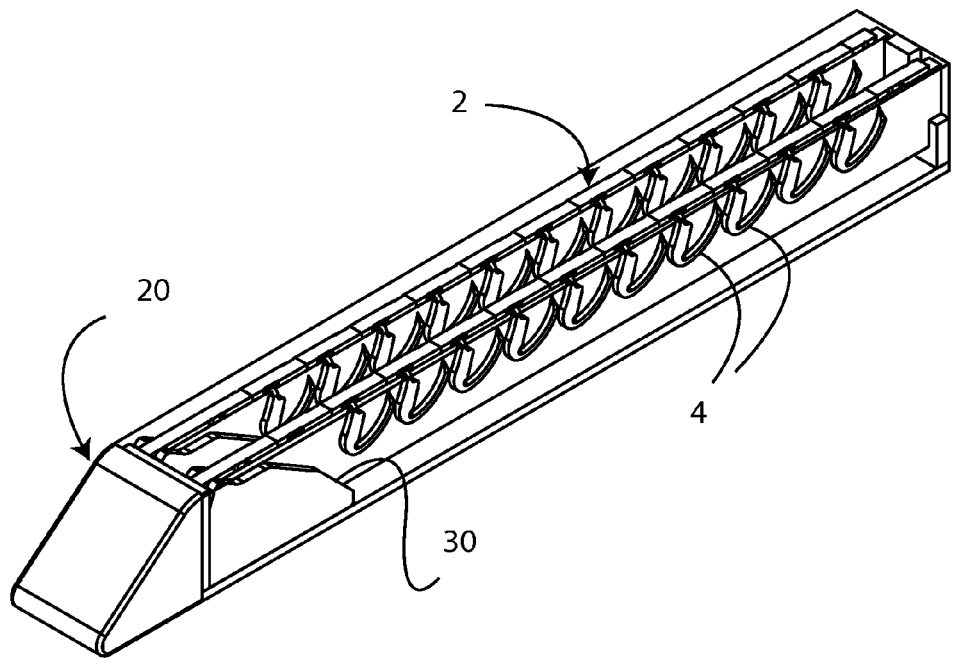
FIG. 2 is a perspective cutaway view of the exemplary feeder belt of FIG. 1 positioned within a cartridge.
Figure 3:
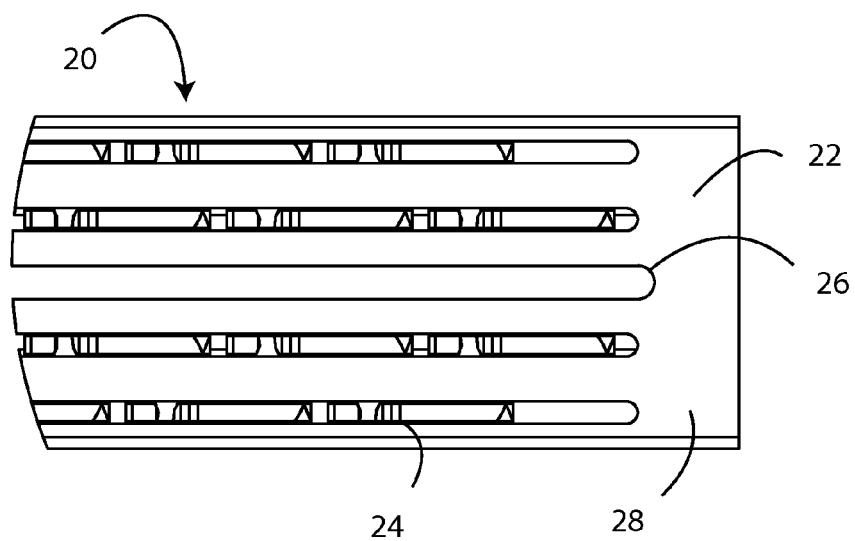
FIG. 3 is a detail top view of the proximal end of the cartridge of FIG. 2.

As seen in FIG. 1, an exemplary feeder belt 2 may be a generally flat and generally linear piece of material that carries a plurality of staples 4. The feeder belt 2 may lie substantially in a single plane. The feeder belt 2 may be flexible, or instead may be rigid. Such a feeder belt 2 may have a proximal end 12 and a distal end 14. Referring also to FIG. 2, a cartridge 20 may hold one or more feeder belts 2. At least one feeder belt 2 may be held entirely within the cartridge 20, for convenience in interchangeability. The cartridge 20 may be configured substantially as set forth in the Endocutter Document, with the exception of the inventive features set forth herein. The one or more feeder belts 2 may be held by the cartridge 20 in any suitable manner. As one example, the proximal end 12 and the distal end 14 of the feeder belt 2 each may be fixed to the cartridge 20. Referring also to FIG. 2A, the cartridge 20 may have an upper surface 22 through which one or more staple slots 24 may be defined. A knife slot 26 may also be defined in the upper surface 22 of the cartridge 20. In order to fix a feeder belt 2 to the cartridge 20, the proximal end of 12 of the feeder belt 2 may be fastened to the upper surface 22 of the cartridge 20 at a connection area 28 proximal to the corresponding slot 24. Similarly, the distal end 14 of the feeder belt 2 may be connected to a similar area distal to the corresponding slot 24. The staples 4 are oriented such that they are deployable through the corresponding staple slot 24. The proximal end 12 of the feeder belt 2 may be fastened to the connection area 28 on the upper surface 22 of the cartridge 20 in any suitable manner. For example, the proximal end 12 of the feeder belt 2 may be welded to, adhered to, pinned or otherwise mechanically connected to, or friction or interference fit to the connection area 28. The distal end 14 of the feeder belt 2 may be connected to the upper surface 22 of the cartridge 20 distal to the corresponding staple slot 24 in a similar or different manner.

Figure 5:
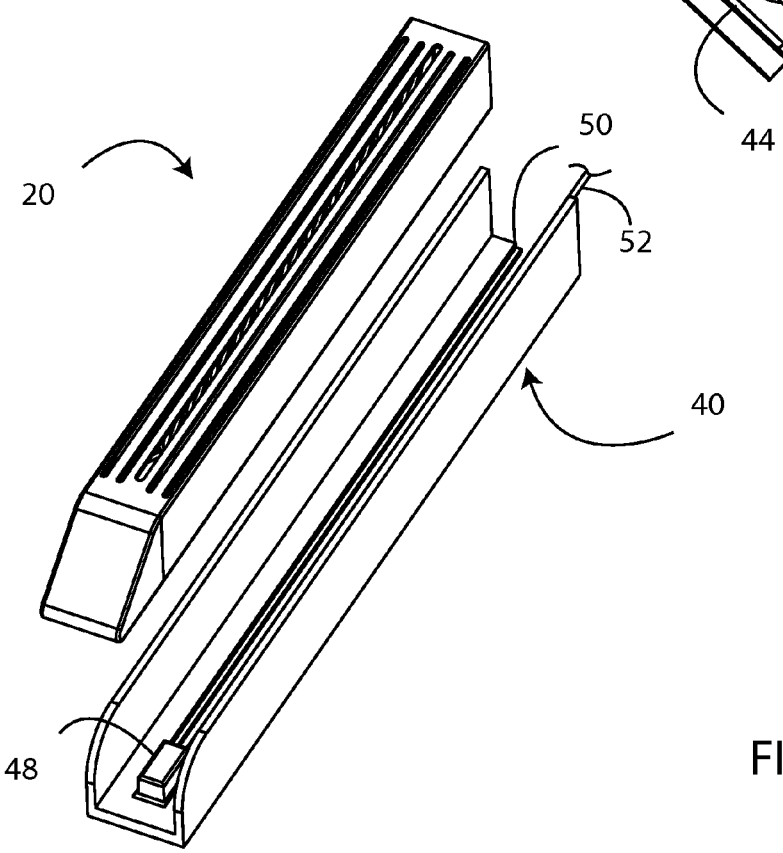
FIG. 5 is a perspective view of the cartridge of FIG. 3 above a corresponding receiver.
Figure 7:
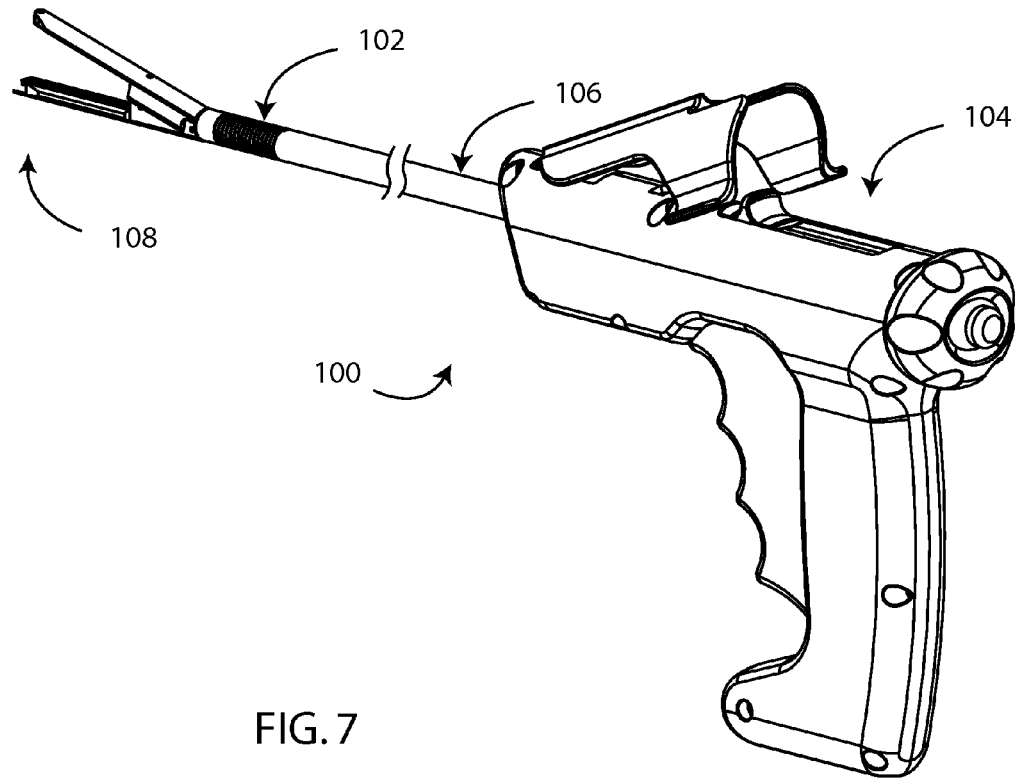
FIG. 7 illustrates a surgical instrument for beneficial use with a staple cartridge.

Referring also to FIG. 7, use of the cartridge 20 may be beneficial for use in a surgical instrument 100 where an articulation 102 is utilized in the instrument proximal to the cartridge 20. For example, the surgical instrument 100 may include a handle 104 from which a shaft 106 extends, where an articulation 102 is located in the shaft 106. Such a surgical instrument 100 may be as described in U.S. patent application Ser. No. 12/400,760, filed on Mar. 9, 2009, which is hereby incorporated by reference in its entirety. An end effector 108 may be connected to the distal end of the shaft 106, distal to the articulation 102. Referring also to FIG. 5, the cartridge 20 is configured to be placed in and held by a receiver 40, which may be part of the end effector 108. By holding each feeder belt 2 inside the cartridge 20, which in turn is held by the end effector 108, no feeder belt 2 crosses the articulation 102, which may simplify construction of the surgical instrument 100. At the same time, the cartridge 20 may be configured to hold fewer staples 4 than described in the Endocutter Document.

Figure 4:
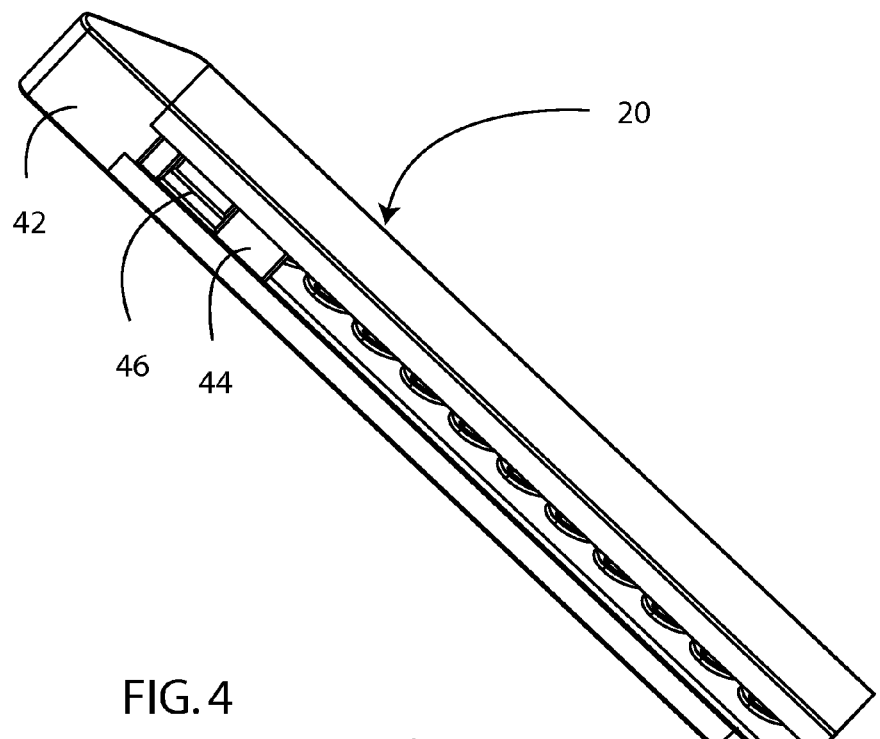
FIG. 4 is a perspective view of the underside of the cartridge of FIG. 3.

The receiver 40 may receive and hold the cartridge 20 in any suitable manner. As one example, the cartridge 20 may be pressure fit into the receiver 40. As another example, the cartridge 20 may snap into or otherwise be affirmatively held in the receiver 40 in a different manner. Referring also to FIG. 4, the underside 42 of the cartridge 20 may include at least one aperture 44 defined therethrough. As set forth in the Endocutter Document, one or more wedges 30 slide relative to the staples 4 in order to deploy them, and the wedges 30 may be fixed to or otherwise connected to a wedge block 44. The wedge block 44 may include a pocket 46 defined in its underside, where that pocket 46 is aligned with the aperture 44. A tab 48 may be located in the receiver 40, and may be a slidable along a channel 50 defined in the lower surface of the receiver 40. One or more cables 52 may extend proximally from the tab 48, and may extend out of the end effector 108 through the shaft 106 to the handle 104. One or more of the cables 52 may pass through the articulation 102 in the shaft 106. The tab 48 is sized and shaped to be received into the pocket 46 of the wedge block 44.

The cartridge 20 may be actuated substantially as set forth in the Endocutter Document. Each wedge 30 may be connected to the wedge block 44. The wedges 30 may initially be in a distal position within the cartridge 20. To actuate the wedges 30, the cable or cables 52 are pulled proximally in response to input from, for example, the handle 104. This motion of the cable or cables 52 causes the tab 48 to move proximally, which in turn moves the wedge block 44 proximally. As the wedge block 44 moves proximally, it slides the wedge or wedges 30 proximally as well. Advantageously, one wedge 30 slides along a corresponding row 10 of staples 4 to sequentially deform staples 4 upward through the corresponding staple slots 24, and then shear staples 4 from the feeder belts 2. A knife (not shown) also may be connected to the wedge block 44, and may slide upward through the corresponding knife slot 26 as set forth in the Endocutter Document.

The wedge block 44 may be actuated to move proximally along a distance such that all of the staples 4 are deformed and then sheared off the corresponding feeder belts 2. If so, the cartridge 20 is configured for a single firing. Alternately, the wedge block 44 may be actuated to move along a distance such that only a subset of the staples 4 are deformed and then sheared off the corresponding feeder belts 2. If so, the cartridge 20 can be reused at least once.

After firing, and after the cartridge 20 is spent such that no staples 4 are left in the cartridge 20 or such that fewer staples 4 are left in the cartridge 20 than the user needs to perform another procedure, the cartridge 20 may be removed from the receiver 40. A new cartridge 20 may then be placed in the receiver 40, in substantially the same manner as described above. In this way, the majority of the surgical instrument 100 may be reused with regard to a patient, while only the cartridge 20 needs to be replaced when spent. Advantageously, the wedges 30 may be contained entirely within the cartridge 20, simplifying the process of removing the cartridge 20 from the receiver 40 and replacing it with a fresh one.

As another example, the feeder belt 2 may form a continuous loop, such as set forth in the Endocutter Document. Such a feeder belt 2 may be held completely within the corresponding cartridge 20. That feeder belt 2 thereby is configured to hold more staples 4 than the two-dimensional feeder belt 2 of FIG. 1, but may be configured to hold fewer staples 4 than described in the Endocutter Document. Such a feeder belt 2 may be advanced substantially as described in the Endocutter Document, or in any other suitable manner. Where the cartridge 20 utilizes such a feeder belt 2, the cartridge 20 advantageously may be fired two or more times before its replacement is needed.

Figure 6:
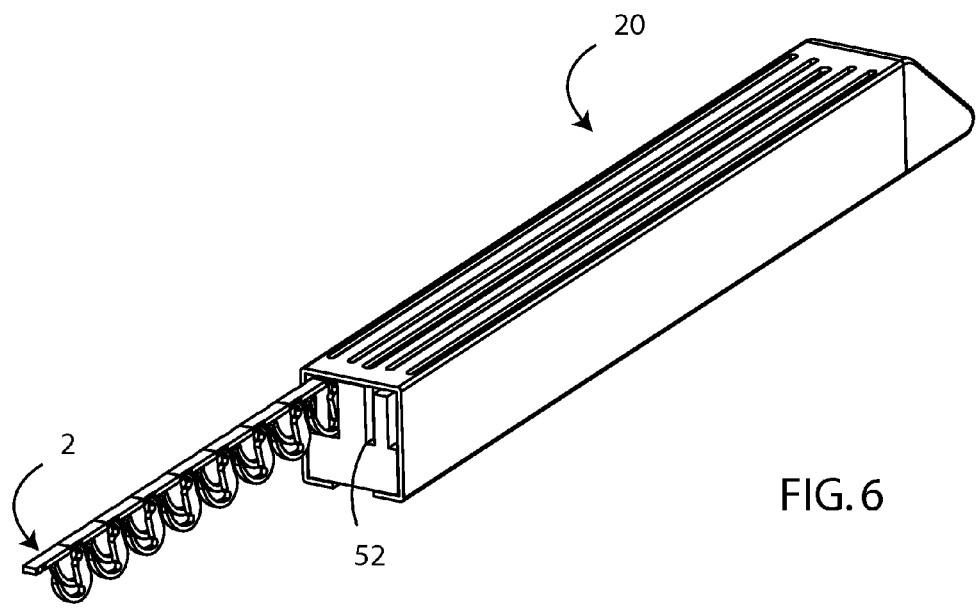
FIG. 6 is a perspective view of a reloadable cartridge utilizing the exemplary feeder belt of FIG. 1.

As another example, the cartridge 20 itself may be reloadable, as shown in FIG. 6. If so, the cartridge 20 may include one or more rear apertures 52 defined in its proximal end. After use, the spent feeder belt 2 may be slid through the corresponding rear aperture 52 and disposed of in a suitable manner. A new feeder belt 2 may then be slid through each corresponding rear aperture 52, and may be held in place in the cartridge 20 in any suitable manner. In this way, even more of the surgical instrument 100 may be reusable in the course of treatment of a single patient.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus for use with a workpiece instrument including a receiver defined therein, comprising:
   at least one feeder belt;
   a plurality of staples integral with and frangibly separable from said feeder belt; and
   a cartridge holding said feeder belt and to which said feeder belt is fixed, said cartridge insertable into the receiver.

2. The surgical apparatus of claim 1, wherein at least one said feeder belt is rigid.

3. The surgical apparatus of claim 2, wherein said cartridge includes an upper surface with at least one staple slot defined therethrough; wherein the proximal end of at least one said feeder belt is fixed to said upper surface of said cartridge proximal to the corresponding said staple slot, and wherein the distal end of that at least one said feeder belt is fixed to said upper surface of said cartridge distal to the corresponding said staple slot.

4. The surgical apparatus of claim 3, wherein said cartridge further comprises a wedge block with a pocket defined therein; wherein said wedge block is slidable within said cartridge.

5. The surgical apparatus of claim 4, further comprising at least one wedge fixed to said wedge block.

6. The surgical apparatus of claim 1, wherein at least one said feeder belt is removable from said cartridge.

7. The surgical apparatus of claim 6, wherein said cartridge includes at least one rear aperture defined in its proximal end, and wherein at least one said feeder belt is removable from said cartridge by sliding said feeder belt proximally through the corresponding said rear aperture.

8. The surgical apparatus of claim 1, wherein each said feeder belt is located entirely within said cartridge.

9. The surgical apparatus of claim 1, wherein said feeder belt is a loop held within said cartridge.

10. A surgical method for utilizing a surgical instrument having a receiver defined therein, comprising:
   providing a cartridge and a feeder belt affixed to said cartridge, wherein a plurality of staples are integral with and frangibly separable from said feeder belt;
   inserting said cartridge into the receiver;
   deforming at least one said staple to a deformed state; and
   frangibly separating at least one said deformed staple from said feeder belt.

11. The surgical method of claim 10, further comprising removing said cartridge from the surgical instrument after said frangibly separating.

12. The surgical method of claim 11, further comprising repeating said deforming and said frangibly separating at least once before said removing.

13. The surgical method of claim 11, further comprising, after said removing, reloading said cartridge with at least one different said feeder belt, and reloading the same said cartridge into said surgical instrument.

14. The surgical method of claim 11, further comprising replacing said cartridge with a different said cartridge after said removing.

15. The surgical apparatus of claim 1, wherein said cartridge is detachable from the receiver.

* * * * *